US00PP16225P2

(12) United States Plant Patent
Westhoff

(10) Patent No.: US PP16,225 P2
(45) Date of Patent: Jan. 31, 2006

(54) ***LOBELIA* PLANT NAMED 'WESLOWAT'**

(50) Latin Name: *Lobelia erinus*
Varietal Denomination: Weslowat

(75) Inventor: Heinrich Westhoff, Südlohn (DE)

(73) Assignee: Josef und Heinrich Westhoff Gartenbau-Spezialkulturen, Südlohn (DE)

( * ) Notice: Subject to any disclaimer, the term of this patent is extended or adjusted under 35 U.S.C. 154(b) by 77 days.

(21) Appl. No.: 10/805,582

(22) Filed: Mar. 20, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Lobelia* plant named 'Weslowat', characterized by its cascading plant habit; freely branching habit with short internodes; continuously and freely flowering habit; densely pubescent leaves; light blue-colored flowers; and relatively tolerant to high temperatures.

1 Drawing Sheet

Botanical classification/cultivar designation: *Lobelia erinus* Weslowat.

BACKGROUND OF THE INVENTION

The present Invention relates to a new and distinct cultivar of *Lobelia* plant, botanically known as *Lobelia erinus*, and hereinafter referred to by the name 'Weslowat'.

The new *Lobelia* is a product of a planned breeding program conducted by the Inventor in Südlohn, Germany. The objective of the breeding program was to develop new *Lobelia* cultivars with continuous flowering, interesting flower colors and tolerance to high temperatures.

The new *Lobelia* originated from a cross-pollination made by the Inventor in 2002 of a proprietary selection of *Lobelia erinus* identified as code number 01P050, not patented, as the female, or seed, parent with a proprietary selection of *Lobelia erinus* identified as code number 01P212, not patented, as the male, or pollen, parent. The new *Lobelia* was discovered and selected by the Inventor from within the resultant progeny from the above-mentioned cross-pollination in a controlled environment in Südlohn, Germany in 2002.

Asexual reproduction since 2002 of the new cultivar by terminal cuttings in a controlled environment in Südlohn, Germany, has shown that the unique features of this new *Lobelia* are stable and reproduced true to type in successive generations.

SUMMARY OF THE INVENTION

The following traits have been repeatedly observed and are determined to be the unique characteristics of 'Weslowat'. These characteristics in combination distinguish 'Weslowat' as a new and distinct cultivar:

1. Cascading plant habit.
2. Freely branching habit with short internodes.
3. Continuously and freely flowering habit.

4. Densely pubescent leaves.
5. Light blue-colored flowers.
6. Relatively tolerant to high temperatures.

Plants of the new *Lobelia* have larger flowers than plants of the female parent, a proprietary selection identified as code number 01P050. In addition, plants of the new *Lobelia* produce flowers that differ in color from the female parent selection. Plants of the new *Lobelia* have foliage with dense pubescence compared to the smooth foliage of plants of the male parent, a proprietary selection identified as code number 01P508. In addition, plants of the new *Lobelia* have thicker stems and lighter blue-colored flowers than plants of the male parent selection.

Plants of the cultivar Weslowat can be compared to the cultivar Weslowei, disclosed in U.S. Plant Pat. No. 12,708. However in side-by-side comparisons conducted in Südlohn, Germany, plants of the cultivar Weslowat and the cultivar Weslowei differed in the following characteristics:

1. Leaves and stems of plants of the new *Lobelia* were more pubescent than plants of the cultivar Weslowei.
2. Plants of the new *Lobelia* flowered more continuously than plants of the cultivar Weslowei.
3. Plants of the new *Lobelia* and the cultivar Weslowei differed in flower color.
4. Plants of the new *Lobelia* had smaller flowers than plants of the cultivar Weslowei.
5. Plants of the new *Lobelia* were more tolerant to high temperatures than plants of the cultivar Weslowei.

Plants of the new *Lobelia* can also be compared to plants of the cultivar Weslobigblue, disclosed in U.S. Plant Pat. No. 12,634. However, in side-by-side comparisons conducted in Südlohn, Germany, plants of the new *Lobelia* differed from plants of the cultivar Weslobigblue in the following characteristics:

1. Plants of the new *Lobelia* were more compact than plants of the cultivar Weslobigblue.
2. Leaves and stems of plants of the new *Lobelia* were more pubescent than leaves and stems of plants of the cultivar Weslobigblue.

3. Plants of the new *Lobelia* had smaller flowers than plants of the cultivar Weslobigblue.
4. Flowers of plants of the new *Lobelia* lighter blue in color than flowers of plants of the cultivar Weslobigblue.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the actual colors of the new *Lobelia*.

The photograph at the top of the sheet comprises a close-up view of a typical individual flower of 'Weslowat'.

The photograph at the bottom of the sheet comprises side view of a typical plant of 'Weslowat' grown in a hanging basket container.

DETAILED BOTANICAL DESCRIPTION

Plants of the cultivar Weslowat have not been observed under all possible environmental conditions. The phenotype may vary somewhat with variations in environment such as temperature and light intensity without, however, any variance in genotype.

In the following description, color references are made to The Royal Horticultural Society Colour Chart, 2001 Edition, except where general terms of ordinary dictionary significance are used. Plants used for the description were grown in a glass-covered greenhouse and conditions that closely approximate commercial production conditions during the spring and summer in Südlohn, Germany. Plants used for the above-mentioned photographs and following description were grown as one plant per 12-cm container or three plants per 25-cm hanging basket container. During the production of the plants, day temperatures ranged from 20 to 25° C. and night temperatures ranged from 16 to 18° C. Plants were pinched once during the production period by removing about 1 to 2 cm of the uppermost apical growing tip. Plants were about 20 weeks from planting when the photographs and description were taken.

Botanical classification: *Lobelia erinus* cultivar Weslowat.

Parentage:

*Female parent*.—Proprietary selection of *Lobelia erinus* identified as code number 01P050, not patented.

*Male parent*.—Proprietary selection of *Lobelia erinus* identified as code number 01P212, not patented.

Propagation:

*Type cutting*.—Terminal vegetative cuttings.

*Time to initiate roots*.—About 18 to 21 days at 20° C.

*Time to develop roots*.—About 20 to 28 days at 20° C.

*Root description*.—Fine, fibrous and well-branched.

Plant description:

*Plant form/habit*.—Cascading flowering plants with light blue-colored flowers. Lateral shoots outwardly spreading; plants uniform with dense foliage. Foliage and stems are very pubescent. Freely branching with lateral branches forming at every node; dense and bushy plant habit. Pinching plants enhances branching. Moderately vigorous growth habit.

*Usage*.—Appropriate for hanging baskets, window boxes and patio containers.

*Plant height* (*soil level to top of plant plane*).—About 12 cm.

*Plant length* (*soil level to lateral branches apices*).—About 47 cm.

*Plant diameter*.—About 40 to 45 cm.

*Lateral branch description*.—Length: About 19.2 cm. Diameter: About 1.1 mm. Internode length: About 2 cm. Texture: Densely pubescent. Color: 138A.

*Foliage description*.—Arrangement: Alternate; simple. Basal leaves: Length: About 5 cm. Width: About 3.6 cm. Shape: Nearly round. Apex: Retuse. Base: Attenuate. Margin: Slightly crenate. Petiole length: About 1.7 mm. Mid-plant leaves: Length: About 3.8 cm. Width: About 2.1 cm. Shape: Ovate. Apex: Rounded. Base: Attenuate. Margin: Crenate. Petiole length: About 8.6 mm. Apical leaves: Length: About 2.8 cm. Width: About 5.8 mm. Shape: Oblanceolate. Apex: Slightly acute. Base: Attenuate. Margin: Mostly entire. Petiole length: Petioles not observed. Texture, all leaves, upper and lower surfaces: Densely pubescent. Color, all leaves: Developing foliage, upper surface: 137A. Developing foliage, lower surface: 138B. Fully developed foliage, upper surface: 147A; venation, 147B. Fully developed foliage, lower surface: 147B; venation, 147B.

Flower description:

*Flower type and habit*.—Flowers arranged singly at lateral apices. Flowers held mostly outwardly. Flowers persistent. Older flowers are overgrown by new flowers and foliage. Freely and continuously flowering. Flowers not fragrant.

*Flower shape*.—Tubular with three larger lower petals and two upright petals.

*Natural flowering season*.—Spring until frost in the autumn.

*Flower longevity on the plant*.—Longevity of individual flowers is highly dependent on weather conditions; typically three to ten days.

*Flower size*.—Diameter: About 1.7 cm. Depth (height): About 1.6 cm. Tube length: About 7 mm. Throat diameter, distal end: About 3.9 mm. Tube diameter, proximal end: About 2.7 mm.

*Flower buds*.—Length: About 1.1 cm. Diameter: About 2.5 mm. Shape: Oblong. Color: Base, 145C to 145D; towards the apex, close to 145C to 145D; color becoming closer to 115C to 115D with development.

*Petals*.—Arrangement: Single whorl of five petals, fused; three larger lower petals and two smaller upper petals. Three lower petals: Shape: Obovate. Length, above throat: About 1 cm. Width: About 5.4 mm. Two upper petals: Shape: Spatulate. Length, above throat: About 5.3 mm. Width: About 2 mm. Upper and lower petals: Apex: Cuspidate to rounded. Margin: Entire. Texture, upper and lower surfaces: Smooth, satiny. Color: When opening, upper surface: 97A. When opening, lower surface: 97A to 97B. Fully opened, upper surface: 97A; towards the base of the lower petals, close to 155D. Fully opened, lower surface: 97B to 97C. Throat: 97C to 97D; stripes, 144A, and spots, 95B. Tube: 96D to 97B; spots, 96C and 144B.

*Sepals*.—Arrangement: Single whorl of five sepals, star-shaped calyx. Length: About 5.8 mm. Width: About 9.2 mm. Shape: Triangular. Apex: Acute. Margin: Entire. Texture, upper and lower surfaces: Smooth. Color, upper and lower surfaces: 147A.

*Peduncles*.—Appearance: Wiry. Length: About 2 cm. Diameter: About 7 mm. Texture: Densely pubescent. Color: 137A.

*Reproductive organs.*—Stamens: Quantity per flower: About five, fused. Anther length: About 1.9 mm. Anther diameter: About 1 mm. Anther color: 186A and 186C. Pollen amount: Moderate. Pollen color: 8A. Pistils: Quantity per flower: One. Pistil length: About 6 mm. Stigma shape: Two-parted, ovate. Stigma texture: Pubescent. Stigma color, immature: 186A. Stigma color, mature: 81B. Style length: About 3.6 mm. Style color: 145A. Ovary color: 145A. Seed/fruit: Seed and fruit production have not been observed.

Disease/pest resistance: Plants of the new *Lobelia* have not been noted to be resistant to pathogens and pests common to *Lobelia*.

Temperature tolerance: Plants of the new *Lobelia* have been observed to tolerate temperatures ranging from 2 to 30° C.

It is claimed:

1. A new and distinct cultivar of *Lobelia* plant named 'Weslowat', as illustrated and described.

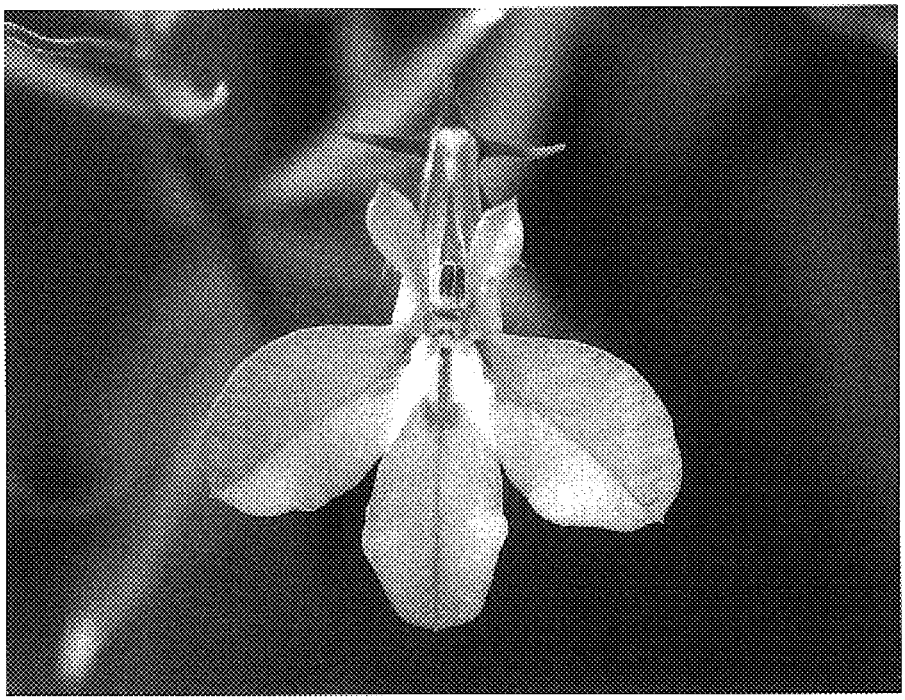
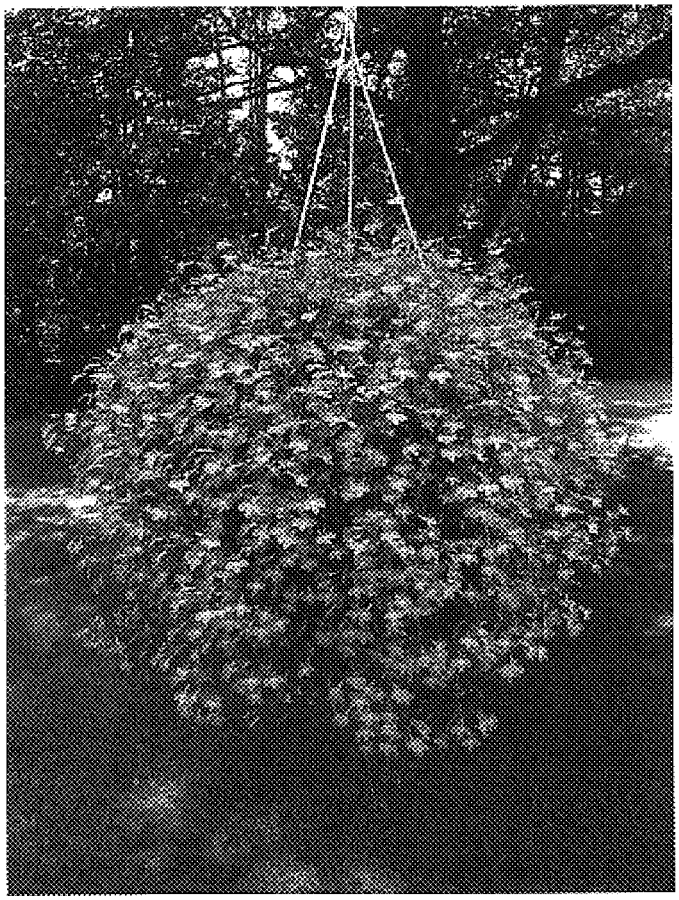

* * * * *